United States Patent
Blanchard et al.

(10) Patent No.: US 10,751,308 B2
(45) Date of Patent: Aug. 25, 2020

(54) COMPOSITION FOR PREVENTING OR REDUCING TRANSEPIDERMAL WATER LOSS

(71) Applicant: NESTEC S.A., Vevey (CH)

(72) Inventors: Carine Blanchard, Le Mont-sur-Lausanne (CH); Chiara Nembrini, Oron-la-Ville (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/071,530

(22) PCT Filed: Jan. 26, 2017

(86) PCT No.: PCT/EP2017/051583
§ 371 (c)(1),
(2) Date: Jul. 20, 2018

(87) PCT Pub. No.: WO2017/129643
PCT Pub. Date: Aug. 3, 2017

(65) Prior Publication Data
US 2019/0029981 A1    Jan. 31, 2019

(30) Foreign Application Priority Data
Jan. 26, 2016 (EP) .................... 16152740

(51) Int. Cl.
| *A61K 31/19* | (2006.01) |
| *A61K 31/702* | (2006.01) |
| *A23L 33/12* | (2016.01) |
| *A23L 33/135* | (2016.01) |
| *A61P 17/00* | (2006.01) |
| *A61K 35/00* | (2006.01) |

(52) U.S. Cl.
CPC .............. *A61K 31/19* (2013.01); *A23L 33/12* (2016.08); *A23L 33/135* (2016.08); *A61K 31/702* (2013.01); *A61P 17/00* (2018.01); *A23V 2002/00* (2013.01); *A23V 2200/318* (2013.01); *A23V 2200/3204* (2013.01); *A23V 2250/1884* (2013.01); *A61K 2035/115* (2013.01)

(58) Field of Classification Search
CPC ................. A61K 31/19; A61K 31/702; A61K 2035/115; A23L 33/12; A23L 33/135; A23V 2250/1884; A23V 2200/318; A23V 2200/3204; A23V 2002/00; A61P 17/00
See application file for complete search history.

(56) References Cited

U.S. PATENT DOCUMENTS

| 5,662,954 A * | 9/1997 | Joiner ................. A23L 2/52 426/384 |
| 2010/0074871 A1 * | 3/2010 | Russell ............... A61K 31/702 424/93.4 |
| 2011/0020395 A1 * | 1/2011 | Benyacoub .......... A61K 35/747 424/204.1 |

FOREIGN PATENT DOCUMENTS

| CN | 102090560 A | 6/2011 |
| CN | 103797021 A | 5/2014 |
| CN | 104546880 | 4/2015 |
| EP | 1597978 | 11/2005 |
| EP | 2455387 | 5/2012 |
| JP | 2000319171 | 11/2000 |
| WO | 2006115412 | 11/2006 |
| WO | WO-2007105945 A2 * | 9/2007 ........... A61K 31/702 |

OTHER PUBLICATIONS

Ishiguro et. al., Eur. J. Immunol., 2007, Molecular Immunology, vol. 37, pp. 2309-2316 (Year: 2007).*
Wang et al., "Advances of study on the Relationship between Short-Chain Fatty Acids in the Intestine and Allergic Diseases", Chinese Journal of Microecology, vol. 25, Issue No. 1, Jan. 2013, pp. 104-108.
China Patent Office Communication for Application No. 201780005466. 2, dated Jun. 1, 2020, 16 pages.

* cited by examiner

*Primary Examiner* — Sarah Pihonak
(74) *Attorney, Agent, or Firm* — K&L Gates LLP

(57) ABSTRACT

The present invention relates to the use in a pregnant or lactating woman of SFCA ingredient, SCFA originating ingredients or mixtures thereof for preventing and/or treating trans epidermal water loss (TEWL) and/or TEWL-associated disorders and/or enhance skin barrier function in the off-spring or breast-fed infant.

13 Claims, 2 Drawing Sheets

COMPOSITION FOR PREVENTING OR REDUCING TRANSEPIDERMAL WATER LOSS

CROSS REFERENCE TO RELATED APPLICATIONS

The present application is a National Stage of International Application No. PCT/EP2017/051583, filed on Jan. 26, 2017, which claims priority to European Patent Application No. 16152740.3, filed on Jan. 26, 2016, the entire contents of which are being incorporated herein by reference.

FIELD OF INVENTION

The present invention relates to the use in maternal administration of short chain fatty acids (SCFA) ingredients for preventing or treating transepidermal water loss (TEWL) and/or TEWL-associated disorders or/and enhancing skin barrier function in the off-spring or breast-fed infant.

BACKGROUND

The primary function of the skin is to protect the body against environmental stresses and to prevent against dehydration.

TEWL is a term used in dermatology to characterize the loss of water that passes from the inside of a body through the epidermal layer (skin) to the surrounding atmosphere via diffusion and evaporation processes.

TWEL is also the most physiological readout to assess compromised skin barrier function as it is well established that an impaired skin barrier eventually leads to loss of water throughout the skin.

Transepidermal water loss can have genetic and/or environmental etiology. Specifically, it can be the results of a genetic polymorphism leading to a decrease in protective protein expression and thus compromised skin barrier. Skin inflammation, mainly caused by an external irritant, can also lead to water loss. Both genetic and environmental components can together or separately lead to excessive transepidermal water loss and ultimately trigger different TEWL-associated skin diseases that range from dry skin to more severe conditions such as eczema.

Transepidermal water loss having a genetic component can lead to dry skin or reactive skin or eczema. When this water loss has an environmental component and is for instance linked to the exposure to an allergen through the skin, this can lead to an allergic eczema/atopic dermatitis, i.e. an eczema accompanied by allergic sensitization.

For the establishment of eczema and reactive skin a genetic predisposition (polymorphism in genes such as filaggrin gene or SPINK5) and an irritant such as for example soap, transpiration, stress, cold, wool, allergens are usually necessary for the development of the disease. Subjects suffering from eczema show reactions of the skin against agents that usually do not cause any skin irritation in healthy subjects (like soap, cold, transpiration, stress, wool, allergen).

In TEWL-associated disorders, the normal water loss rate is increased due to a diminished barrier function of the epidermis. A TEWL-associated disorder is thus mainly characterized by the symptoms of a dehydrated epidermis like dry or scaly skin. In humans, TEWL associated disorders are often associated with atopic dermatitis (also called eczema) and/or reactive skin (like winter rashes). Other diseases with an increased TEWL and skin inflammatory condition comprise chronological aging, injury, infection and/or severe damage as in the case of burns, psoriasis, and a range of inflammatory skin conditions such as atopic diathesis in rosacea and perioral dermatitis.

Measurement of TEWL is thus a way to measure loss of water through the epidermal layer (skin) and is considered as one of the best marker for skin barrier function and consequently for the risk of developing a skin associated disease.

Indeed, an increased TEWL at 2 days and 2 months in infant predicts for eczema at 1 year of age. (*Skin barrier dysfunction measured by transepidermal water loss at 2 days and 2 months predates and predicts atopic dermatitis at 1 year*: Maeve Kelleher et al. JACI 2014.) and the enhancement of skin barrier function from birth to 6 months significantly decrease (50%) the risk of developing eczema. (*Emollient enhancement of the skin barrier from birth offers effective atopic dermatitis prevention*. Simpson E L. JACI 2014).

TEWL measurement can also be used to assess and quantify the clinical outcome of a skin disease.

It is therefore the object of the present invention to provide a composition for maternal administration for the prevention or treatment of transepidermal water loss and/or TEWL-associated disorders and/or to enhance the skin barrier function in the off-spring or breast-fed infant. Preferentially, this composition is administered to a pregnant and/or lactating woman.

SUMMARY

It is the object of the invention to provide new and alternative solutions to the problem of preventing or treating transepidermal water loss and/or TEWL-associated disorders and/or enhancing skin barrier function of infants. It has been surprisingly found that short chain fatty acids (SCFA) are useful, when administered to a pregnant or lactating woman, in preventing or treating transepidermal water loss and/or TEWL-associated disorders and/or in enhancing the skin barrier function and/or for the prevention of eczema in the offspring or in the infant of the lactating mother.

The evaluation of ingredients which are useful in the treatment or prevention of transepidermal water loss and/or TEWL associated disorders and/or for enhancing skin barrier function was assessed in new born mice whose mothers received such ingredients during pregnancy.

Therefore, the invention relates to a composition for maternal administration before and during pregnancy and/or during lactation comprising SCFA ingredients or SCFA originating ingredients, for use in the prevention and/or treatment of transepidermal water loss and/or of a TEWL-associated disorder and/or for enhancement of barrier function of the skin (i.e. epidermal layer) in the offspring. The use of said composition results, in the offspring, in the prevention or treatment of transepidermal water loss, in an increase of skin barrier protection, in particular in the prevention or treatment of a TEWL-associated disorder, in the prevention or treatment of eczema and/or in the prevention or treatment of reactive skin.

The maternal composition can be administered orally, via enteral or parenteral route.

The maternal composition can also be a nutritional composition, a pet nutritional composition, an oral nutritional supplement, or a pharmaceutical product. In particular the composition is adapted to pregnant and lactating mother.

The maternal nutritional composition can be selected from the group consisting of a beverage product, a yoghurt product, a fermented milk, a fruit juice, or a cereal bar, powdered milk composition, a pouch, a powder to spray on the food, a liquid drop to swallow.

The maternal nutritional composition can be a food for specific medical purposes such as a powder to dissolve in liquid or a pills or capsules as a health care nutritional composition for oral feeding, a nutritional product for enteral feeding or a parenteral feeding product. Additionally, the maternal composition can contain only the SCFAs as a nutritional supplement.

In one aspect, the present invention provides a maternal composition as above described for use in therapeutically preventing and/or treating transepidermal water loss (TEWL) and/or TEWL-associated disorders and/or for use in enhancing skin barrier function, in the off-spring or breast-fed infant of the woman to whom the maternal composition is administered.

In another aspect, the present invention provides the non-therapeutic use of a maternal composition according to the present invention for preventing and/or treating transepidermal water loss (TEWL) and/TEWL associated disorders and/or enhance skin barrier function in the off-spring or breast-fed infant of the pregnant or lactating woman to whom the maternal composition is administered.

DEFINITIONS

Figure 1:
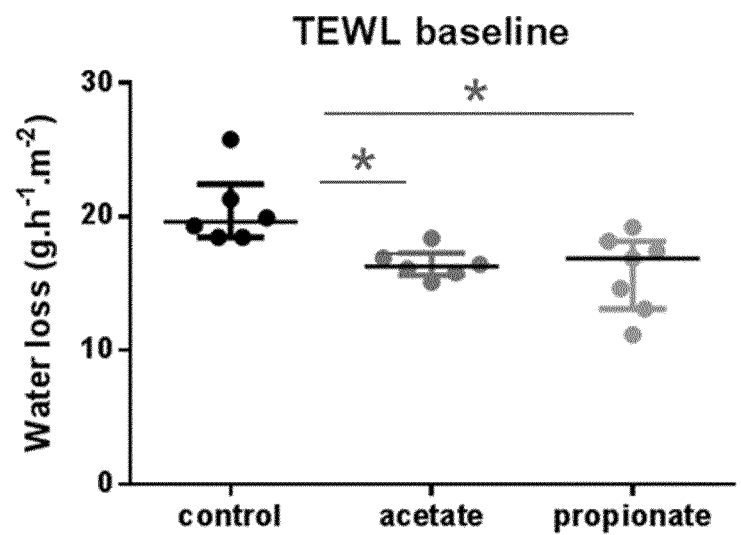
FIG. 1 shows transepidermal water loss in 3-days old pups born from mothers receiving SCFA in drinking water during pregnancy (Results from Example 1).

The term "infant" indicates a child under the age of 18 months.

The term "offspring infant" or "off-spring" indicates according to the present invention a child under the age of 18 months which was born by a mother who took maternal composition according to the present invention either pre-conceptional and/or during pregnancy and/or during lactation.

The term "breast-fed infant" or "breast-fed off-spring" indicates a child under the age of 18 months which was born by a mother who took maternal composition according to the present invention pre-conceptional and/or during pregnancy and while breast-feeding such infant.

"Transpidermal water loss (TEWL)" is defined as the the quantity of water that passes from inside a body (animal or plant) through the epidermal layer (skin) to the surrounding atmosphere via diffusion and evaporation processes. Symptoms of TEWL are, in particular, a dry or scaly skin.

"Transpidermal water loss (TEWL) measurement" according to the present invention means measurement of TEWL in the offspring. TEWL measurements are of great importance in evaluating barrier functionality of the epidermal layer. Normal rates of TEWL are compromised due to injury, infection and/or severe damage as in the case of burns. Damage to the stratum corneum and superficial skin layers not only results in physical vulnerability, but also results in an excess rate of water loss. Normal rates of TEWL in human adult forearm are $7 \pm 3$ g·h$^{-1}$·m$^{-2}$. In newborn TEWL is higher due to immaturity of the skin. In the sense of the invention, rates of TEWL of 3 g·h$^{-1}$·m$^{-2}$ above control matched population are considered to be abnormal and indicative of a disorder of the skin (i.e., the epidermal layer).

"TEWL-associated disorders" are the skin conditions in which TEWL is abnormally increased. These include but are not limited to: dry skin, eczema/atopic dermatitis, reactive skin, burns, psoriasis, dermatitis, rosacea and idiopathic skin inflammation. The etiology of these conditions is frequently associated with genetic polymorphism leading to the decreased expression of protein highly involved in the skin barrier function such as protein encoded by genes of the epidermal differentiation complex (eg filaggrin, involucrin, sprr) and protein involved in tight junctions. Therefore, the invention relates to the prevention or treatment of eczema or reactive skin or the symptoms caused by reactive skin, burns, psoriasis, dermatitis, rosacea and idiopathic skin inflammation, dry skin or scaly skin.

"Barrier function" or "skin barrier protection" or "skin barrier function" is the function of the (epidermal) barrier to prevent the transition of agents, allergens, microorganisms, or water through the epidermal layer.

The terms "Eczema" and "atopic dermatitis" (AD) are used interchangeably in the present invention. Eczema is an inflammatory, chronically relapsing, non-contagious and pruritic (itch causing) skin disorder. The skin of a patient with eczema overreacts easily to irritants, food, and environmental allergens and becomes red, flaky and very itchy (becomes a reactive skin). It also becomes vulnerable to surface infections caused by bacteria. The skin on the flexural surfaces of the joints is often affected in human subjects. Symptoms may vary from person to person but they are usually present as a red, inflamed, and itchy rash and can quickly develop into raised and painful bumps. The skin tends to be more sensitive and may thicken, crack, become dry or scale. Epidermal barrier dysfunction is considered to be an explanation on the physiopathology of atopic dermatitis. Changes in certain genes encoding structural proteins, epidermal proteases and protease inhibitors predispose to a defective epidermal barrier and increase the risk of developing atopic dermatitis. The strong association between both genetic barrier defects and environmental insults to the barrier with atopic dermatitis suggests that epidermal barrier dysfunction is a primary event in the development of this disease.

Enhancing barrier function with topical treatment is a current clinical approach to prevent or treat eczema. An important indicator of barrier function is TEWL. It is assumed that TEWL can be reduced in the off-spring by the administration to the pregnant mother of SCFA or ingredients giving rise to SCFA in the human body and thereby eczema can be treated. Without being bound to any theory, we believe that the effect may be mediated by improving the tight junction system of the skin.

Within the context of the present invention, the expression "Short chain Fatty Acid (also SCFA)" identifies propionic acid, formic acid, acetic acid, butyric acid, valeric acid, iso-butyric acid and iso-valeric acid and/or physiologically acceptable salts thereof (such as for example calcium, potassium, sodium, magnesium, ammonium salts of propionate, formate, acetate, butyrate, valerate, iso-butyrate and iso-valerate) or mixtures thereof.

SCFA are mainly synthesized by fermentation and are naturally found in some food such as milk fat or vinegar. In humans SCFA are produced in the gastrointestinal tack in the intestine; the main production site is the colon due to microbial density. SCFA are metabolites of fermentable material in the colon and derived mainly from complex carbohydrates or fermentable fibers such as lactose, prebiotics and oligosaccharides, but can also derived from protein fermentation.

Within the context of the present invention, the expression "Short chain Fatty Acid (also SCFA) Ingredient" identifies ingredients essentially constituted by SCFA as above defined as well as ingredients naturally containing SCFA as above defined. Non-limiting examples of this second category of SCFA ingredients are for example some dairy products and vinegar.

Within the context of the present invention the expression "SCFA originating ingredient" identifies ingredients which by mammal/animal/microbial metabolism give rise to SCFA in the human/animal body of the subject assuming them. Non-limiting examples of SCFA originating ingredients are:
  glycerol derivatives such as mono-, di- and tri-acyl glycerol derivatives incorporating one or more SCFAs, such as for example tributirin, triacetin, tripropionin;
  phospholipid derivatives such as phophatidylcholine, phosphatidylethanolamine, phosphatidylserine, phospatidylethanol in which one or more acyl chains consist of SCFA;
  organic esters of SCFA, such as for example methyl, ethyl, propyl or iso-propyl esters (non-limiting examples of such SFCA organic esters are: ethyl butanoate, ethyl propionate, ethyl acetate etc); such esters may be naturally occurring or may be obtained via chemical reactions for example by condensation of a SCFA and an appropriate alcohol (for example ethylic alcohol);
  fibers or protein incorporating SCFAs, such as for example butyrated or acetylated fibers, for example butyrated or acetylated starch;
  fermentable fibers, such as for example fermentable oligosaccharides and starches. The fermentable fibers can include but are not restricted to pectins, mucilages, gums, galacto-oligosaccharides, oligofructan, inulin, polyfructoses, arabinoglactans, hemicelullose, oligosaccharides or mixtures of thereof.

The SCFA originating ingredient may generate SCFA according to different mechanisms occurring in the human or animal body.

For example, glycerol and triglycerides derivatives incorporating SCFAs may generate SCFA in human or animal intestine, by digestion occurring in the small intestine.

For example, fermentable fibers may generate SCFA in human or animal intestine, particularly in the colon, by fermentation achieved by microbiota naturally present therein.

For example, fibers or starch incorporating SCFAs may generate or liberate SCFA in human or animal intestine, by digestion occurring in the small or large intestine followed by fermentation of the non-digested part of the fiber achieved by microbiota naturally present in the colon.

The SFCA ingredients and/or the SCFA originating ingredients may be incorporated in the maternal compositions of the invention in the form of a free ingredient or they may be incorporated in the compositions in encapsulated form for example to mitigate the impact of flavors.

For the purposes of this invention, the terms "treating" or "treatment" mean to decrease or alleviate the symptoms suffered by a mammal, in particular an animal or human being, especially the symptoms of a skin disorder and/or assist in the management of a skin disorder. The terms "treatment" and "treating" further mean to promote or aid recovery of the skin for example to improve the appearance and condition of the skin.

The terms "prevention" or "preventing" mean to stop the onset of symptoms or to reduce the severity of such symptoms suffered by a mammal, in particular an animal or human being. In addition the terms "prevention" or "preventing" mean to delay the onset of symptoms.

As used herein the term "enhancing the skin barrier function" means that the barrier function of the skin is strengthened. This skin barrier function is assessed by measuring transepidermal water loss in dermatology clinics. "Enhancing the skin barrier function" thus decreases the transition of agents, allergens, microorganisms, or water through the epidermal layer. In particular, this enhancement of barrier function may be mediated by a reduction of the interstitial room between the epidermal cell layers. This may be effected by increasing the number of tight junctions or/and increasing the quality of the tight junctions between the epidermal cells and/or increased expression of protein of the epidermal differentiation complex (such as filaggrin, sprr, NICE, involucrin, loricrin).

As used herein, the term "nutritional composition" includes, but is not limited to, complete nutritional compositions, partial or incomplete nutritional compositions, nutritional supplements, and disease or condition specific nutritional compositions.

As used herein, "Maternal composition" refers to a composition and/or nutritional composition for maternal administration in a mammal, in particular a woman, which may occur pre-, during, and/or post-pregnancy. The administration of said composition to the mother starts pre-conceptional, during pregnancy or during lactation for prevention. Alternatively, administration in the mother can start when the breastfed infant is symptomatic for treatment. The administration of said maternal composition to the mother pre-conceptional, during pregnancy or during lactation prevents and/or treats transepidermal water loss (TEWL) and/or TEWL-associated disorders and/or enhance skin barrier function in the off-spring or breast-fed infant of the woman to whom the maternal composition is administered.

The term "nutritional supplement", or "dietary supplement", as used herein, refers to a nutritional product that provides nutrients to an individual that may otherwise not be consumed in sufficient quantities by said individual. Supplements can for example be provided in the form of a pill, a tablet a lozenger, a chewy capsule or tablet, a tablet or capsule, or a powder supplement that can for example be dissolved in water or sprinkled on food. Most preferred is a powder supplement that can be dissolved in liquid or sprinkled on food, most preferably dissolved in water. Such supplements typically provide the selected nutrients while not representing a significant portion of the overall nutritional needs of the subject. Typically they do not represent more than 0.1%, 1%, 5%, 10% or 20% of the daily energy need of the subject.

The term "food product", as used herein, refers to any kind of product that may be safely consumed by a human or animal.

Said food product may be in solid, semi-solid or liquid form and may comprise one or more nutrients, foods or nutritional supplements. For instance, the food product may additional comprise the following nutrients and micronutrients: a source of proteins, a source of lipids, a source of carbohydrates, vitamins and minerals. The composition may also contain anti-oxidants, stabilizers (when provided in solid form) or emulsifiers (when provided in liquid form).

The term "functional food product" as used herein, refers to a food product providing an additional health-promoting or disease-preventing function to the individual.

The term "dairy products", as used herein, refers to food products produced from animals such as cows, goats, sheep, yaks, horses, camels, and other mammals. Examples of dairy products are low-fat milk (e.g. 0.1%, 0.5% or 1.5% fat), fat-free milk, milk powder, whole milk, whole milk products, butter, buttermilk, buttermilk products, skim milk, skim milk products, high milk-fat products, condensed milk, creme fraiche, cheese, ice cream and confectionery products, probiotic drinks or probiotic yoghurt type drinks.

The term "pharmaceutical formulation" or "pharmaceutical composition" as used herein, refers to a composition comprising at least one pharmaceutically active agent, chemical substance or drug. The pharmaceutical formulation may be in solid or liquid form and can comprise at least one additional active agent, carrier, vehicle, excipient, or auxiliary agent identifiable by a person skilled in the art. The pharmaceutical formulation can be in the form of a tablet, capsule, granules, powder, liquid or syrup. The term "beverage product" as used herein, refers to a nutritional product in liquid or semi-liquid form that may be safely consumed by an individual.

The term "pet food product" as used herein refers to a nutritional product that is intended for consumption by pets. A pet, or companion animal, as referenced herein, is to be understood as an animal selected from dogs, cats, birds, fish, rodents such as mice, rats, and guinea pigs, rabbits, etc.

DETAILED DESCRIPTION OF THE INVENTION

The section headings serve to clarify the subject matter and should not be interpreted to limit the subject matter. If ranges of values are disclosed each individual value is considered to be covered by the range, in particular, each integer number. If not noted otherwise, values in % relate to weight/weight (w/w) values.

It has been surprisingly found that SCFA administered to a pregnant or lactating woman are useful for decreasing transepidermal water loss and/or prevent or treat TEWL-associated disorders and/or for enhancing skin barrier protection in the offspring or breast-fed infant of the lactating mother.

This finding was made in a mice model for eczema that allowed determining TEWL. Therefore, it can be concluded that SFCA can be used in the treatment or prevention of transepidermal water loss, of TEWL-associated disorders, eczema or, in general, for enhancing skin barrier function. Without wanting to be bound to any theory it is believed that SCFA increase epidermal barrier function by increasing the number or quality of tight junctions in the epidermal cell layer.

Maternal Compositions

The compositions of the invention comprises at least one SCFA ingredient, or one SCFA originating ingredient as above defined or mixtures thereof.

The maternal composition can comprise at least one, at least two, at least three, or at least four different SCFA ingredients or SCFA originating ingredient as above defined.

The maternal composition can comprise at least one, at least two, at least three, or at least four different SCFA ingredient, SCFA originating ingredients or mixtures thereof.

The composition can comprise only SCFA (100%).

In one embodiment, SCFA is selected in the group consisting of: propionic acid, formic acid, acetic acid, butyric acid, valeric acid, iso-butyric acid and iso-valeric acid; physiologically acceptable salts thereof (such as for example calcium, potassium, sodium, magnesium, ammonium salts of propionate, formate, acetate, butyrate, valerate, iso-butyrate and iso-valerate; and mixtures thereof.

In another embodiment, SCFA is selected in the group consisting of: propionic acid, acetic acid, butyric acid; physiologically acceptable salts thereof (such as for example calcium, potassium, sodium, magnesium, ammonium salts of propionate, acetate, butyrate; and mixtures thereof.

When SCFA are included in a nutritional composition, the composition can comprise 1 to 100%, 10 to 90%, 20 to 80% 30 to 70%, 40 to 60% of SCFA ingredient and/or SCFA originating ingredient.

In one embodiment, the SCFA originating ingredient is selected in the group consisting of:

glycerol derivatives such as mono-, di- and tri-acyl glycerol derivatives incorporating one or more SCFAs, such as for example tributirin, triacetin, tripropionin;

phospholipid derivatives such as phophatidylcholine, phosphatidylethanolamine, phosphatidylserine, phospatidylethanol in which one or more acyl chains consist of SCFA;

organic esters of SCFA, such as for example methyl, ethyl, propyl or iso-propyl esters (non-limiting examples of such SFCA organic esters are: ethyl butanoate, ethyl propionate, ethyl acetate etc); such esters may be naturally occurring or may be obtained via chemical reactions for example by condensation of a SCFA and an appropriate alcohol (for example ethylic alcohol);

fibers or protein incorporating SCFAs, such as for example butyrated or acetylated fibers, for example butyrated or acetylated starch;

fermentable fibers, such as for example fermentable oligosaccharides and starches. The fermentable fibers can include but are not restricted to pectins, mucilages, gums, galacto-oligosaccharides, oligofructan, inulin, polyfructoses, arabinoglactans, hemicelullose, oligosaccharides or mixtures of thereof;

or mixtures thereof.

In one embodiment, the SCFA originating ingredient is a fermentable fiber. In a further embodiment, SCFA originating ingredient is a fermentable fiber which is selected in the group consisting of: pectins, mucilages, gums, galacto-oligosaccharides, oligofructan, inulin, polyfructoses, arabinoglactans, hemicelullose, oligosaccharides and mixtures of thereof.

Formulations

The above described maternal compositions can be formulated in liquid or solid form. The compositions can further comprise at least one additional active agent, carrier, vehicle, excipient, or auxiliary agent identifiable by a person skilled in the art upon reading of the present disclosure.

The maternal composition can be in the form of a nutritional composition, oral nutritional supplement or pharmaceutical product. A nutritional composition, nutritional supplement or pharmaceutical product can comprise the composition or kit of the invention.

All ingredients of the composition can be admixed together or alternatively the composition can be provided in the form of a kit of parts wherein ingredients or groups of ingredients are provided separately and are intended to be consumed together by the woman.

Preferably, the maternal composition of the invention is administered to a woman desiring to get pregnant, for example during at least 1, 2, 3 or 4 months preceding the pregnancy or desired pregnancy. When the composition is to be administered to a pregnant or lactating woman, the composition is preferably administered for at least 4, preferably at least 8, more preferably at least 12, more preferably at least 16, more preferably at least 20, more preferably at least 24, more preferably at least 28, even more preferably at least 36 weeks during pregnancy and or lactation.

The administration of said maternal composition to the mother pre-conceptional, during pregnancy or during lactation prevents and/or treats transepidermal water loss (TEWL) and/or TEWL-associated disorders and/or enhance skin barrier function in the off-spring or breast-fed infant of the woman to whom the maternal composition is administered.

The maternal composition can be in any form that is suitable to administer all the ingredients to the woman. For example it can be in the form of a powdered nutritional composition to be reconstituted in milk or water, a food product, a functional food product, a drink (beverage), a dairy product, a pharmaceutical formulation, a pet food product, a nutritional supplement or a nutraceutical.

Nutritional Composition

A complete nutritional composition (i.e., those which contain all the essential macro and micro nutrients) can be used as a sole source of nutrition for the subject assuming it. Patients can receive 100% of their nutritional requirements from such complete nutritional composition. A partial or incomplete nutritional composition does not contain all the essential macro and micro nutrients and cannot be used as a sole source of nutrition for the subject assuming it.

Partial or incomplete nutritional compositions can be used as a nutritional supplement. An oral supplemental nutritional composition contains mainly or exclusively the essential active ingredients of the claimed composition (the SCFA) and can be consumed in addition to the regular nutrition of the subject assuming it.

A nutritional composition may additional comprise the following nutrients and micronutrients adapted to pregnancy or lactation:
1) a source of proteins;
2) a source of lipids containing or including functional fatty acids such as omega-3 and/or omega-6 polyunsaturated fatty acids (DHA, DGLA, ETA, EPA, GLA, SDA), oil containing polyunsaturated fatty acids or a combination of thereof;
3) a source of carbohydrates;
4) vitamins and minerals. The composition may also contain anti-oxidants, stabilizers (when provided in solid form) or emulgators (when provided in liquid form).

In a further embodiment, the nutritional composition may comprise minerals such as sodium, potassium, calcium, phosphorus, magnesium, chloride, iron, zinc, copper, manganese, fluoride, chromium, molybdenum, selenium, iodine or any combination thereof.

In a further embodiment the nutritional composition comprises further vitamins such as Vitamin A, Vitamin E, Vitamin C, Vitamin B1, Vitamin B2, pantothenic Acid, Vitamin B6, Vitamin B12, Niacin, Folic Acid, Biotin and Choline or any combination thereof.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, *Haemophilus, Moraxella* and Staphylococci.

In a still further embodiment, the nutritional composition is a food for specific medical purposes such as a health care nutritional composition for oral feeding, and/or a nutritional product for enteral or parental feeding. In the latter case it will only include ingredients which are suitable for parenteral feeding. Ingredients that are suitable for parental feeding are known to the person skilled in the art. In particular, a parental feeding composition will contain the SCFA ingredient or SCFA originating ingredient in pure or substantially pure form but the composition can also comprise other ingredients that are known to be suitable for parenteral nutrition.

Kits

The above compositions may also be provided as kits. In those kits the all or a part of the ingredients of the above described compositions are provided in a separate (i.e. not mixed) form. A kit of the invention can comprise the SCFA ingredient, SCFA originating ingredients or mixtures thereof on the one hand and any other ingredients on the other hand in separate form. A kit of the invention can comprise at least two or three SCFA ingredient, SCFA originating ingredients or mixtures thereof provided in a separate form. In an alternative embodiment, the kits can comprise each of the ingredients of the above described composition in a separate form.

Therapeutical Uses and Methods

The maternal composition or the kit of the invention can be used in the prevention or treatment of transepidermal water loss, and/or prevention or treatment of TEWL-associated disorders, and/or prevention or treatment of a skin disorder characterized by a TEWL which is increased compared to a subject not suffering from the disorder, and/or to enhance the skin barrier function, in the off-spring and/or in the breast-fed infant of the lactating mother.

In one embodiment, the maternal composition or the kit of the invention can be used in the treatment and/or prevention of eczema or reactive skin or for enhancing skin barrier function (i.e. epidermal barrier function). The composition or the kit can prevent and/or treat an increase of TEWL. The composition or the kit can prevent an increase of TEWL so that the TEWL value in a subject stays substantially identically or close to the TEWL of a subject not suffering from the disorder.

A normal TEWL measurement in adult human (e.g. forearm) and animals such as rodents is $7 \pm 3$ $g \cdot h^{-1} \cdot m^{-2}$. Normal value in infant depend on the age of the infant the maturity of the skin. An abnormal TEWL measurement is defined as 3 $g \cdot h^{-1} \cdot m^{-2}$ above the TEWL measurement of the control population. Thus, reducing TEWL of 3 $g \cdot h^{-1} \cdot m^{-2}$ to a previous TEWL level that was greater than 10 $g \cdot h^{-1} \cdot m^{-2}$ (e.g. 10.5, 11, 12, 13, 14, 15, 20, 25) is considered to relate to a treatment of a TEWL disorder. In particular, the reduction of a previous TEWL level that was greater than 10 $g \cdot h^{-1} \cdot m^{-2}$ a by 0.5, 1.0, 1.5, 2.0, 3.0, 4.0, 5.0 or 10.0 to a value that is closer to or in the range of $7 \pm 3$ $g \cdot h^{-1} \cdot m^{-2}$ is considered to relate a treatment of TEWL.

The composition or the kit of the invention can also be used in a method for therapeutical prevention and/or treatment of a skin disorder characterized by a TEWL which is increased compared to a subject not suffering from the disorder.

The compositions and kits can be provided in a form that is suitable for oral administration and then be administered accordingly. Oral administration is preferred. Administration can start pre-conceptional, during pregnancy or lactation for prevention. Alternatively, administration in the mother can start when the breastfed infant is symptomatic for treatment. Administration is performed daily, 1 to 6 days per week, 2 to 5 days per week, 3 to 4 days per week, and for a duration of minimum 1 week to up to 3 years. Administration can occur 1 time per day, twice per day or up to 4 times per day.

In an embodiment, the composition is intended for consumption by a human subject, i.e. woman prior or during pregnancy or a woman during lactation.

In another embodiment, the composition is intended for consumption by an animal, preferably a cat or a dog.

Non-Therapeutic Uses and Methods

The maternal composition or the kit of the invention can be used non-therapeutically in the prevention or treatment of transepidermal water loss, and/or prevention or treatment of TEWL-associated disorders, and/or prevention or treatment of a skin disorder characterized by a TEWL which is increased compared to a subject not suffering from the disorder, and/or to enhance the skin barrier function, in the off-spring and/or in the breast-fed infant of the lactating mother. In one embodiment, the maternal composition or the kit of the invention can be used non therapeutically in the treatment and/or prevention of eczema or reactive skin or for enhancing skin barrier function (i.e. epidermal barrier function). The composition or the kit can prevent and/or treat an increase of TEWL.

The composition or the kit of the invention can also be used in a method for therapeutical prevention and/or treatment of a skin disorder characterized by a TEWL which is increased compared to a subject not suffering from the disorder.

The compositions and kits can be provided in a form that is suitable for oral administration and then be administered accordingly. Oral administration is preferred.

Administration can start pre-conceptional, during pregnancy or lactation for prevention. Alternatively, administration in the mother can start when the breastfed infant is symptomatic for treatment. Administration is performed daily, 1 to 6 days per week, 2 to 5 days per week, 3 to 4 days per week, and for a duration of minimum 1 week to up to 3 years. Administration can occur 1 time per day, twice per day or up to 4 times per day.

In an embodiment, the composition is intended for consumption by a human subject, i.e. woman prior or during pregnancy or a woman during lactation.

In another embodiment, the composition is intended for consumption by an animal, preferably a cat or a dog.

Methods of Production

A method for producing the above described composition is provided and comprises providing at least one of the above described SCFA ingredient or SCFA originating ingredient or a mixture thereof, adding optionally at least one further ingredient selected from the group consisting of fat, protein, carbohydrate or physiologically acceptable excipients, adding optionally at least one nutrient or micronutrient, adding a carrier or/and water.

Those skilled in the art will understand that they can freely combine all features of the present invention disclosed herein. In particular, features described for different embodiments of the present invention may be combined. Further advantages and features of the present invention are apparent from the figures and examples.

EXAMPLES

Example 1: Maternal Administration of SCFA Decreases Transepidermal Water Loss in the Offspring Breeding pairs were set up with 1 Balb/c male and 2 Balb/c female mice.

From day 1 of pregnancy, female mice received 200 mM sodium acetate or sodium propionate ad libitum in drinking water. These doses correspond to 0.05-0.1 and 0.05-0.08 g/mouse/day, respectively. Control female mice received regular drinking water.

Cages were monitored from day 18-24 for litters. Regular drinking water was recommenced in the mothers as soon as pups were born. 6-7 pups per group were included in the experiment.

Transepidermal water loss was measured at day 3 after birth (baseline TEWL) by the TEWLmeter method and given in $g \cdot h^{-1} \cdot m^{-2}$.

As it can be observed from results shown in FIG. 1, administration of SCFA such as acetate or propionate to pregnant mothers significantly decreased transepidermal water loss in their offspring in the first days after birth.

Example 2: Fermentable Fiber Administration in Pregnant Mice Decreases Transepidermal Water Loss in the Offspring Breeding pairs were set up with 1 Balb/c male and 2 Balb/c female mice.

From day 1 of pregnancy, female mice received a diet enriched with 30% inulin. A diet enriched at 30% with the non-fermentable fiber cellulose was fed to control female mice.

Cages were monitored from day 18-24 for litters. Regular diet containing a mix of fibers at 4% was recommenced in all mothers as soon as pups were born. 5 pups per group were included in the experiment.

Transepidermal water loss was measured at day 5 after birth (baseline TEWL) by the TEWLmeter method and given in $g \cdot h^{-1} \cdot m^{-2}$.

Figure 2:
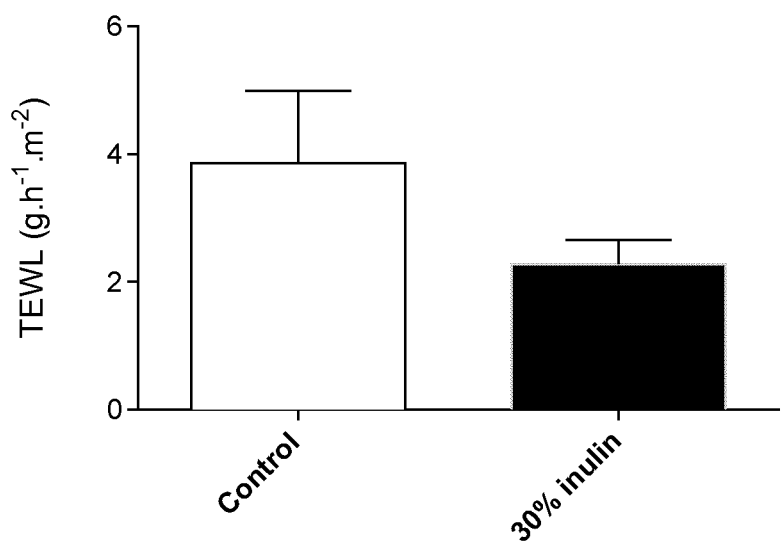
FIG. 2 shows transepidermal water loss in 5-days old pups born from mothers receiving a diet comprising fermentable fiber inulin during pregnancy (Results from Example 2).

As it can be observed from results shown in FIG. 2, administration of inulin decreased transepidermal water loss in their offspring in the first days after birth when compared to a control diet not comprising fermentable fibers.

Example 3: Administration of Fermentable Fibers to Adult Mice Increases SCFA

Balb/c mice were fed from weaning (day 21 after birth) for 4 weeks with a diet enriched with 30% of the fermentable fiber inulin or with a control diet containing 30% cellulose.

Figure 3:
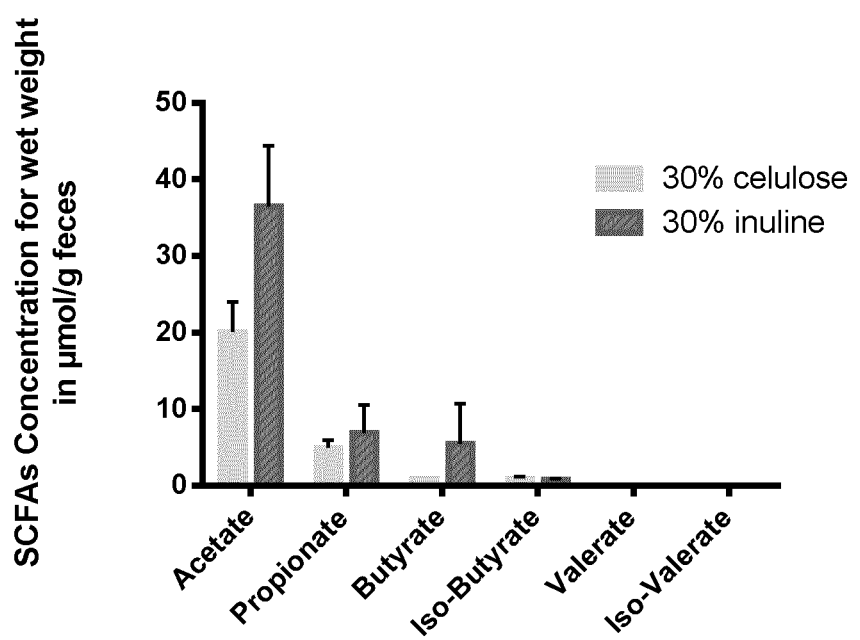
FIG. 3 shows SFCA measurement in adult mice administered with fermentable fibers (Results from Example 3).

Feces were collected at 4 weeks after weaning and the presence of SCFA was measured by Gas-Liquid Chromatography (GLC; amounts of SCFA in µmol/g wet weight). The following SCFA were measured: acetate, propionate, butyrate, valerate, iso-butyrate and iso-valerate and results are reported in FIG. 3.

The measure was made based on the following protocol: SCFA in an acid solution (pH 2.0 to 20 3.0) were separated on a GLC column coated with a polar stationary phase. This allowed for minimal preparation of the sample (no derivatisation) and straightforward basic FID detection. SCFA were extracted from feces using an acid phosphate buffer containing HgCl2.

Increased SCFA production was observed in feces of inuline fed mices compared to cellulose fed mice. Accordingly, is is expected that increase SCFA, and more specifically acetate and butyrate, also in a pregnant woman is associated with a reduction of TWEL in the offspring.

Without wishing to be bound by theory, this suggests that a transfer of SCFA or of a secondary species derived from SCFA to the fetus might occur and imprints the skin physiology of the pups to have an enhanced skin barrier function.

The invention claimed is:

1. A method for preventing or treating transepidermal water loss (TEWL) and/or TEWL-associated disorders in an off-spring or a breast-fed infant of a mother, the method comprising administering to the mother while pregnant and/or while lactating a maternal composition comprising a component selected from the group consisting of acetate, propionate, and a mixture thereof, and the component is 10 to 90 wt. % of the maternal composition.

2. The method according to claim 1, wherein the method prevents or treats TEWL-associated disorders.

3. The method according to claim 1, wherein the administration is during pregnancy of the mother.

4. The method according to claim 1, wherein the maternal composition is administered orally.

5. The method according to claim 1, wherein the maternal composition further comprises polyunsaturated fatty acids.

6. The method according to claim 1, wherein the maternal composition further comprises probiotics.

7. The method according to claim 1, wherein the maternal composition further comprises polyunsaturated fatty acids and probiotics.

8. The method according to claim 1, wherein the maternal composition is in a form selected from the group consisting of a nutritional composition, an oral nutritional supplement and a pharmaceutical product.

9. The method according to claim 8, wherein the maternal composition is selected from the group consisting of a beverage product, a yoghurt product, fermented milk, a fruit juice, and a cereal bar.

10. The method according to claim 1, wherein the component is 20 to 80 wt. % of the maternal composition.

11. The method according to claim 1, wherein the component is 30 to 70 wt. % of the maternal composition.

12. The method according to claim 1, wherein the component is 40 to 60 wt. % of the maternal composition.

13. The method according to claim 1, wherein the component is acetate, and the maternal composition further comprises inulin.

* * * * *